(12) United States Patent
Vesey et al.

(10) Patent No.: US 6,777,222 B1
(45) Date of Patent: Aug. 17, 2004

(54) ANTIBODIES TO CRYPTOSPORIDIUM

(75) Inventors: Graham Vesey, New South Wales (AU); Christopher Weir, New South Wales (AU); Keith Leslie Williams, New South Wales (AU); Martin Basil Slade, New South Wales (AU); Duncan Veal, New South Wales (AU)

(73) Assignees: Macquarie Research Ltd., Sydney (AU); Sydney Water Corporation, Sydney (AU)

( * ) Notice: Subject to any disclaimer, the term of this patent is extended or adjusted under 35 U.S.C. 154(b) by 0 days.

(21) Appl. No.: 09/424,048

(22) PCT Filed: May 19, 1998

(86) PCT No.: PCT/AU98/00368

§ 371 (c)(1),
(2), (4) Date: Feb. 24, 2000

(87) PCT Pub. No.: WO98/52974

PCT Pub. Date: Nov. 26, 1998

(30) Foreign Application Priority Data

May 19, 1997 (AU) ............................................. PO6962
Jul. 25, 1997 (AU) ............................................. PO8242

(51) Int. Cl.[7] ....................... C12N 1/10; A61K 39/395; A61K 39/00
(52) U.S. Cl. ............................. 435/258.1; 424/141.1; 424/151.1; 424/178.1; 424/265.1
(58) Field of Search .......................... 424/141.1, 151.1, 424/178.1, 265.1; 435/258.1

(56) References Cited

PUBLICATIONS

McDonald et al., Characteristics and specificity of hybridoma antibodies against oocysts antigens of *Cryptosporidium parvum* from man, Parasite Immun. 13:251–259 (1991).

Tilley et al., Multiple oral inoculations with *Crypotosporidium parvum* as a means of immunization for production of monoclonal antibodies, FEMS Microbiol. Lett. 113:235–240 (1993).

Korich et al., Development of a test to assess *Crytosporidium parvum* oocysts viability: correlation with infectivity potential, AWWA Res. Found. and Am. Water Works. Assoc. (1993).

Bonnin, A. et al., "Characterization of Microneme Antigens of *Cryptosporidium parvum*", Infection and Immunity, May 1991, pp. 1703–1708.

Bonnin, A. et al., "A New Antigen of *Cryptosporidium parvum* Micronemes Possesing Epitodes Cross–Reactive with Macrogamete Granules", Parasitology Research vol. 79, 1993, pp. 8–14.

Bonnin, A. et al., "Monoclonal Antibodies Identify A Subset of Dense Granules in *Cryptosporidium parvum* Zoites and Gamonts", Journal of Eukaryotic Microbiology vol. 42, 1995, pp. 395–401.

McDonald, V. et al., "Localization of Parasite Antigens in *Cryptosporidium parvum*–infected Epithelial Cells Using Monoclonal Antibodies", Parasitology vol. 110, 1995, pp. 259–268.

Ortega–Mora, L.M. et al., "Identification of *Cryptosporidium parvum* Oocyst/Sporozoite Antigens Recognized by Infected and Hyperimmune Lambs", Veterinary Parasitology 53, 1994, pp. 159–166.

Peterson, C. et al., "Identification and Initial Characterization of Five *Cryptosporidium parvum* Sporozoite Antigen Genes", Infection and Immunity, vol. 60, No. 6, Jun. 1992, pp. 2343–2348.

Riggs, M.W. et al., "Bovine Antibody Against *Cryptosporidium parvum* Elicits a Circumsporozoite Precipitate–like Reaction and Has Immunotherapeutic Effect Against Persistent Cryptosporidiosis in SCID Mice", Infection and Immunity, vol. 62, No. 5, May 1994, pp. 1927–1939.

*Primary Examiner*—Rodney P Swartz
*Assistant Examiner*—Khatol S Shahnan-Shah
(74) *Attorney, Agent, or Firm*—Morgan, Lewis & Bockius LLP

(57) ABSTRACT

A method of producing IgG1 subclass antibodies reactive to the surface of *Crystosporidium oocysts*, the method comprising: (a) separating at least a protion of the Cryptosporidium oocyst wall from the internal sporozoites to form an oocyst-wall preparation; (b) treating the separated oocyst-wall preparation so as to obtain an oocyst antigen preparation capable of eliciting a detectable IgG1 immune response in an animal to the surface of the oocyst; (c) immunizing an animal with the oocyst antigen preparation so as to elicit an IgG1 immune response in the animal; and (d) obtaining from the animal IgG1 antibodies reactive to the surface of Cryptosporidium oocysts. IgG1 antibodies reactive to the surface of Cryptosporidium oocysts.

36 Claims, 4 Drawing Sheets

ANTIBODIES TO CRYPTOSPORIDIUM

This is a U.S. National Phase Application under 35 U.S.C. 371 of International Application PCT/AU98/00368 (filed May 19, 1998) and claims priority to Australian Application PO6962 (filed May 19, 1997) and Australian Application PO8242 (filed Jul. 25, 1997), all of which are incorporated herein in their entirety.

TECHNICAL FIELD

The present invention relates to antibodies to Cryptosporidium and methods to raise suitable Cryptosporidium-specific antibodies in animals.

BACKGROUND PRIOR ART

The protozoan parasite Cryptosporidium is amongst the most common pathogens responsible for diarrhoeal disease in humans. Infection occurs when Cryptosporidium oocysts shed in the faeces of infected individuals are ingested by new hosts. Recently, several large outbreaks of cryptosporidiosis have occurred in which drinking water has been identified as the source of infection. Surveys have shown that many surface water supplies are contaminated with Cryptosporidium oocysts.

Laboratory methods used to detect Cryptosporidium often involve the use of antibodies to this organism. Typical methods used to analyse water samples for the presence of this organism include microscopy and cytometry or a combination of these techniques. Flow cytometric methods involve staining of samples with a fluorescently labelled monoclonal antibody specific to the surface of Cryptosporidium oocysts and then analysis with a sorter flow cytometer. Particles with the fluorescence and light scatter characteristics of Cryptosporidium oocysts are sorted onto a microscope slide and examined manually using epifluorescence microscopy to confirm their identity as oocysts. This confirmation step is necessary because with a single antibody the cytometer is unable to distinguish oocysts from all other particles present in water samples. The particles that the cytometer can mistake as oocysts are autofluorescent particles such as algae or particles that non-specifically bind the oocyst-specific antibody.

Analysis-only flow cytometers are available which are simple to operate and relatively inexpensive. These cytometers are unable to perform sorting. To enable the detection of Cryptosporidium oocysts using an analysis-only cytometer the discrimination achieved by the cytometer must be improved so that non-oocyst particles are not mistaken as oocysts. The present inventors have shown previously that it is possible to detect a single specific microorganism in turbid water samples with an analysis cytometer if the microorganism is labelled with two different antibodies.

Unfortunately, the antibodies for Cryptosporidium presently available are not ideal due their stickiness and there is a need for more specific and reactive antibodies to the surface of Cryptosporidium oocysts. Monoclonal antibodies (mAbs) that are specific to the surface of Cryptosporidium oocysts are used for detecting Cryptosporidium in clinical and environmental samples. All available mAbs that bind to the surface of Cryptosporidium oocysts are of the immunoglobulin M (IgM) or IgG3 subclass. Monoclonal antibodies of the IgG1 subclass would be preferable because they usually show less non-specific binding. Such mAbs would be more suitable in methods currently used for the detection and identification of Cryptosporidium. Unfortunately, past attempts by workers in the field to produce IgG1 monoclonal antibodies to Cryptosporidium have been unsuccessful or not substantiated (Smith, 1994; MacDonald et al., 1991). It is generally considered that due to the antigenic characteristics of this organism, this class of antibody is not produced by infected or immunised animals (Smith, 1994).

In WO 97/08204 filed by the present inventors, monoclonal antibodies to a range of Cryptosporidium oocyst antigens were developed. Whole or excysted oocysts that were exposed to various treatments were used as antigens. From a total of eight fusions that included screening several thousand hybridomas only one hybridoma was identified that was specific to the surface of Cryptosporidium oocysts. This monoclonal antibody was of the IgM immunological subclass.

The present inventors have now developed a new method that allows the production of IgG1 antibodies to the surface of Cryptosporidium oocysts.

DISCLOSURE OF INVENTION

In a first aspect, the present invention consists in a method of producing IgG1 subclass antibodies reactive to the surface of Cryptosporidium oocysts comprising: (a) pretreating Cryptosporidium oocysts with a reagent so as to remove the surface layer of the oocysts to form an oocyst antigen preparation; (b) separating the oocysts from the antigen preparation so as to obtain a separated oocyst antigen preparation capable of eliciting a detectable IgG1 immune response in an animal to the surface of the oocyst; (c) immunising an animal with the separated oocyst antigen preparation so as to elicit an IgG1 immune response in the animal; and (d) obtaining from the animal IgG1 antibodies reactive to the surface of Cryptosporidium oocysts.

It will be appreciated that once a suitable immune response has been stimulated in an animal, for example in a laboratory mouse, monoclonal antibodies of IgG1 subclass may be generated by standard techniques from that animal.

In a preferred embodiment of the first aspect of the present invention, the reagent used to prepare the antigen preparation is a detergent, preferably the detergent is sodium dodecyl sulphate (SDS). One suitable pretreatment involves boiling the oocysts in the presence of SDS for a sufficient time to generate a suitable antigen preparation. When a concentration of 0.5% (w/v) SDS is used, boiling for 1 hour has been found to be particularly suitable.

Other suitable reagents include urea, detergents such as Triton X-100 or nonident, enzymes such chitinase, oxidising agents such as sodium hypochlorite, sodium periodate, ozone and reducing agents such as mercaptol ethanol and 1,1,1-trichloro-2,2-bis[4-chlorophenyl]ethane (DDT).

The pretreatment removes antigens from the surface of the oocyst in a form that will allow the generation of IgG1 antibodies when injected into an animal.

The animal may be immunised by any technique suitable for eliciting an immune response in an animal. Adjuvants may also be included with the antigen preparation prior to immunising the animal to promote a strong immune response in the animal.

In a further preferred embodiment, the antigen preparation also enhances the production of IgM antibodies when placed in an animal.

In a second aspect, the present invention consists in a method of producing IgG1 subclass antibodies reactive to the surface of Cryptosporidium oocysts, the method comprising:

(a) separating at least a portion of the Cryptosporidium oocyst wall from the internal sporozoites to form an oocyst-wall preparation:
(b) treating the separated oocyst-wall preparation so as to obtain an oocyst antigen preparation capable of eliciting a detectable IgG1 immune response in an animal to the surface of the oocyst;
(c) immunising an animal with the oocyst antigen preparation so as to elicit an IgG1 immune response in the animal; and
(d) obtaining from the animal IgG1 antibodies reactive to the surface of Cryptosporidium oocysts.

The present inventors have found that in order to obtain a suitable oocyst wall antigen preparation, the oocyst wall should be separated from internal sporozoite components. It appears that the internal sporozoite antigens are more immunodominant than oocyst wall antigens and their presence in an antigen preparation may mask the oocyst wall antigens. A mixed antigen preparation will usually result in raising antibodies to the sporozoite antigens.

The separation of the oocyst wall from the internal sporozoite (step (a)) can be achieved by any means. The present inventors have found that causing the oocyst to excyst followed by immuno-separation of the wall components is particularly suitable. Separation can also be achieved by surface labelling of whole oocysts with a ligand, such as biotin, allowing separation of cell wall fragments from internal components by reaction with a reagent reactive to the ligand, such as avidin, on an insoluble matrix or beads. It will be appreciated, however, that other separation methods known to the art would also be suitable. Examples include centrifugation, flow cytometry, density gradient separation, precipitation, immuno-labelling, ligand-binding, biotin-labelling and separation by avidin, and chromatographic separation.

It is not necessary to cause the oocyst to excyst by normal procedures. The oocysts can be freeze-thawed for example to promote initial separation of the wall from the internal sporozoites. Furthermore, the oocyst may be physically broken up by crushing, sonication, or grinding followed by separation.

The treating step (b) can be carried out by any means suitable. In particular, the present inventors have found that physically breaking up the cell wall can produce a good antigen preparation. This can be done by any means but the use of a bead beater is quite suitable.

The treatment removes antigens from the surface of the oocyst wall in a form that will allow the generation of IgG1 antibodies when injected into an animal.

It will be appreciated that once a suitable immune response has been stimulated in an animal, for example in a laboratory mouse, monoclonal antibodies of IgG1 subclass may be generated by standard techniques from that animal.

The animal may be immunised by any technique suitable for eliciting an immune response in an animal. Adjuvants may also be included with the antigen preparation prior to immunising the animal to promote a strong immune response in the animal.

In a further preferred embodiment, the antigen preparation also enhances the production of IgM antibodies when placed in an animal.

As the present inventors have determined methods that allow the production of useful IgG1 antibodies reactive to the surface of Cryptosporidium oocysts. it will be appreciated that similar antibodies to those produced by the present inventors may now be produced from the information and teaching provided herein.

In a third aspect, the present invention consists in substantially isolated IgG1 antibodies reactive to the surface of Cryptosporidium oocysts produced by the method according to the first or second aspects of the present invention.

Preferably, the antibodies are monoclonal antibodies.

In a fourth aspect, the present invention consists in a substantially isolated IgG1 antibody reactive to the surface of Cryptosporidium oocysts, the antibody having the oocyst binding and affinity characteristics of antibody CRY104.

Preferably, the antibody is a monoclonal antibody.

More preferably, the IgG1 monoclonal antibody is produced by clone CRY104.

In a fifth aspect, the present invention consists in the hybridoma clone CRY104.

The production of antibody CRY104 is defined in the specification such that persons skilled in the art will be able to produce other antibodies with Cryptosporidium oocyst binding and affinity characteristics similar to, or the same as, CRY104. CRY104 is recited in the specification as one example of a suitable IgG1 antibody reactive to the surface of Cryptosporidium oocysts that can be obtained from the teaching of the present invention. Accordingly, a sample of CRY104 is not required for a person to carry out the present invention.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood, preferred forms will be described with reference to the following examples and the accompanying drawing.

MODES FOR CARRYING OUT THE INVENTION

MATERIALS AND METHODS

Cryptosporidium oocysts

Figure 1:
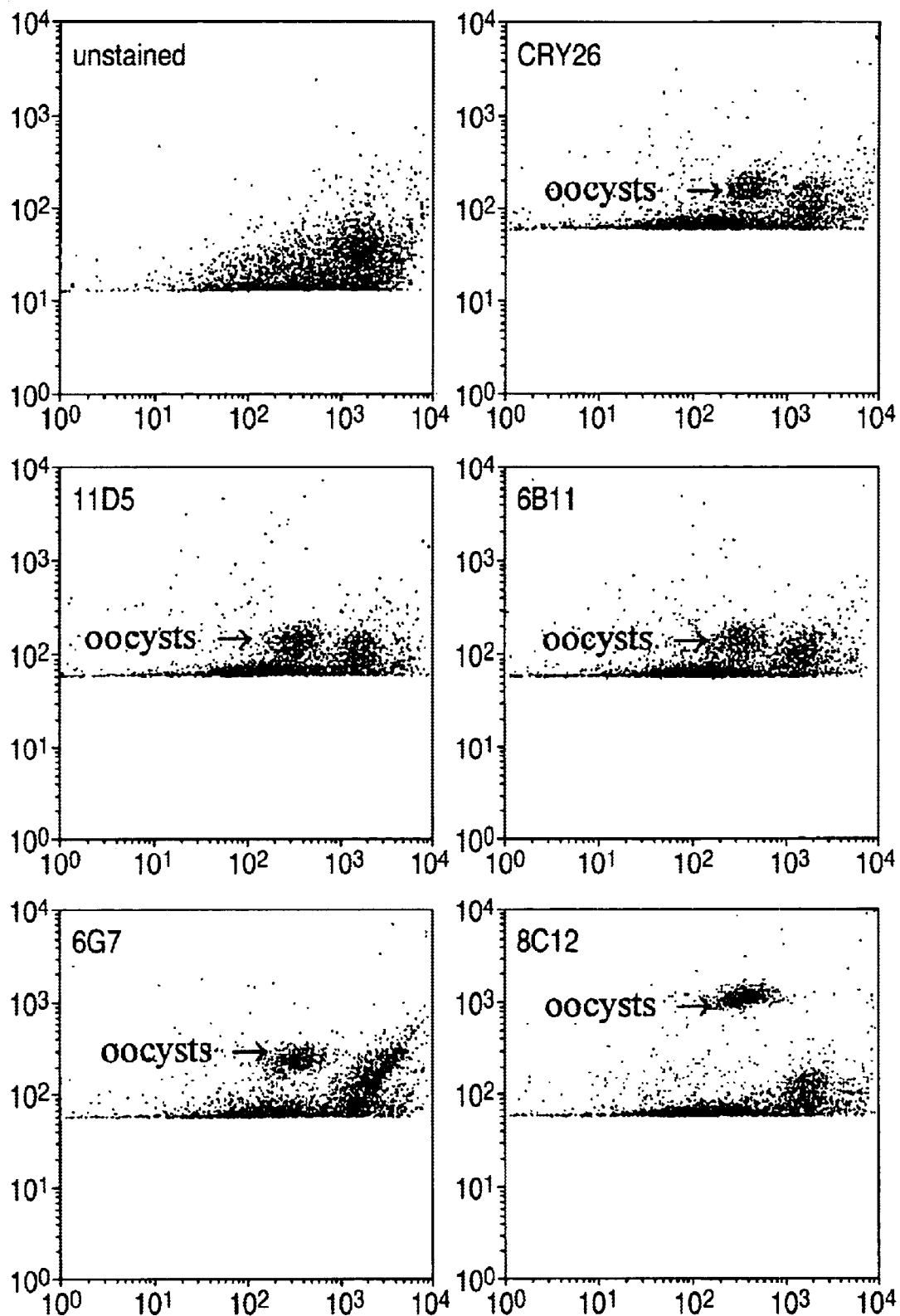
FIG. 1 shows the comparison of monoclonal antibodies for staining oocysts in water samples.

*Cryptosporidium parvum* oocysts were purified from pooled faeces of naturally infected neonatal calves in Sydney. Faecal samples were centrifuged (2000 g, 10 min) and resuspended in water twice and then resuspended in 5 volumes of 1% (w/v) $NaHCO_3$. Fatty substances were then extracted twice with 1 volume of ether, followed by centrifugation (2000 g for 10 min). Pellets were resuspended in water and filtered through a layer of pre-wetted non-adsorbent cotton wool. The eluate was then overlaid onto 10 volumes of 55% (w/v) sucrose solution and centrifuged (2000 g for 20 min). Oocysts were collected from the sucrose interface and the sucrose flotation step repeated until no visible contaminating material could be detected. Purified oocysts were surface sterilised with ice cold 70% (v/v) ethanol for 30 min, washed once in phosphate buffered saline (PBS; Oxoid, Sydney) and stored in PBS at 4° C. for up to 2 weeks.

Antigen Preparation

Surface Extraction

A 2 ml sample of oocysts containing approximately $2 \times 10^9$ oocysts was centrifuged at 13000 g for 1 minute and the supernatant removed and discarded. Oocysts were resuspended in 2 ml of ice cold 0.5% (w/v) SDS and placed in a boiling water bath for one hour. The sample was then centrifuged at 13000 g for 20 minutes to remove the oocysts. The supernatant was carefully removed, mixed with 10 ml of acetone and placed at −20° C. for 8 hours. The sample was then centrifuged at 13000 g for 10 minutes and the supernatant discarded. A small white precipitate was then resuspended in sterile PBS.

The protein concentration was measured using the commercially available Biorad DC protein assay using the standard protocol and bovine serum albumin (BSA) as a standard.

Oocyst Walls

Cryptosporidium oocysts were excysted as described by Robertson et al. (1993). A 1 ml sample of oocysts containing approximately $1 \times 10^9$ oocysts was centrifuged at 13000 g for 1 minute and the supernatant removed and discarded. Oocysts were resuspended in 1 ml of acidified Hank's balanced salt solution (HBSS), pH 2.7, and incubated at 37° C. for 30 min. Samples were then washed and resuspended in 1 ml of HBSS with 100 µl of 1% (w/v) sodium deoxycholate in Hank's minimal essential medium (HMEM) and 100 µl of 2.2% (w/v) $NaHCO_3$ in HBSS, and incubated at 37° C. for 4 h. The sample was then analysed using the Coulter Elite flow cytometer as described previously (Vesey et al., 1997). The population with the lowest forward angle light scatter signal was sorted into test tubes and concentrated by centrifuging at 3000 g for 20 minutes. Concentrated samples were stored at −20° C. in PBS.

Excystation of Oocysts

Excystation was achieved as described above for oocysts walls.

Purification of Oocyst Walls

The oocysts walls were purified from the excysted sample using immuno-magnetic separation. A 0.5 ml aliquot of magnet beads (approximately $5 \times 10^7$ beads) coated with a goat anti-mouse IgM antibody (Dynal Pty Ltd. Australia) were mixed with 10 ml of tissue culture supernatant of a Cryptosporidium oocyst-specific monoclonal antibody CRY26 (Vesey 1996). The beads were incubated at 4° C. for 4 hours and then placed next to a magnet so that the beads were drawn to the bottom of the tube. The supernatant was removed and discarded and the beads resuspended in 10 ml of PBS plus 2% (w/v) bovine serum albumin (BSA; Sigma fraction V)(PBS-BSA). This washing procedure was repeated twice and the beads resuspended in a final volume of 1 ml of PBS-BSA. The beads were then mixed with the sample of excysted oocysts and incubated on a rotary shaker at room temperature for 30 minutes. The tube was placed next to the magnet so that the beads and the attached oocysts were attracted to the bottom of the tube. The supernatant was removed and placed at 4° C. To remove any contaminating sporozoites the beads were gently resuspended in 1 ml of PBS-BSA and then concentrated once more using the magnet. The supernatant was removed and discarded. The beads were resuspended in 1 ml of PBS and vortexed vigorously to unattached the beads from the oocyst walls. The beads were concentrated using the magnet and the supernatant containing the oocyst walls removed and kept on ice. The beads were then added to the original sample of excysted oocysts and the entire procedure repeated 10 times. The 10 samples of purified oocyst walls were then pooled and concentrated by centrifuging at 3000 g for 10 minutes. A fraction of the sample of oocyst walls was analysed using flow cytometry as described previously (Vesey et al., 1997). The sample was analysed in a tube containing an exact number of beads (TrueCount Becton Dickinson, San Hose, USA) to determine the number of oocyst walls.

Breaking Up of Oocysts Walls

Half the sample of oocyst walls were treated to break the walls into small pieces using a FastPrep bead beater (Bio101, CA, USA) fifteen times at maximum speed for 40 second durations. The sample was cooled on ice for 1 minute between each 40 second treatment. The oocyst wall pieces were resuspended into 3 ml of PBS and aliquoted into 200 µl amounts and stored frozen until used.

Immunisation of Mice

Method 1

Five Balb/C female mice were immunised by IP injection with either 200 µg of the oocyst surface extract (group E mice) or $4 \times 10^4$ oocyst walls (group W mice). Antigen preparations were emulsified in Freunds complete adjuvant. Mice were bled prior to receiving the primary injection to provide a negative control. Two further IP injections with the same amount of antigen but emulsified in Freunds incomplete adjuvant were given at 3 week intervals. Mice were bled after the second of these injections to check for immune response. Group E mice were given two final intravenous boosts of 200 µg of antigen were given 3 days and 1 day prior to the fusion.

Method 2

Five Balb/C female mice (group WP) were immunised by IP injection with 200 µl of smashed oocyst wall preparation emulsified in Freunds complete adjuvant. The preparation contained approximately $1 \times 10^6$ oocyst walls. A second group of mice (group WI) were immunised with approximately $1 \times 10^6$ intact purified oocyst walls emulsified in Freunds complete adjuvant. Mice were bled by tail bleeding prior to receiving the primary injection to provide a negative control. Two further IP injections with the same amount of antigen but emulsified in Freunds incomplete adjuvant were given at 3 week intervals. Mice were bled after the second of these injections to check for immune response.

The mouse may be given either IP or IV booster injections to 7 days prior to sacrifice and fusion of spleen cells to assist in the development of appropriate antibodies.

Analysis of Mouse Serum

Samples (approximately 50 µl) of blood was collected by tail bleeding and then centrifuged at 13000 g for 30 seconds. The top layer of serum carefully removed and stored at −20° C. until analysed. Serum was diluted to 1 in 100, 1 in 1000 and 1 in 10.000, in 1% (w/v) bovine serum albumin in PBS (BSA-PBS). Aliquots (50 µl) of diluted serum were mixed with 10 µl of oocyst suspension in PBS (containing approximately $1 \times 10^6$ oocysts) and incubated at room temperature for 20 minutes. Samples were mixed with either 50 μl of goat anti-mouse IgM specific antibody conjugated with FITC (diluted 1 in 50 with BSA-PBS)(Sigma product number) or with 50 μl of goat anti-mouse IgG specific antibody conjugated with PE (diluted 1 in 200 with BSA-PBS)(Sigma). After a further 20 minutes incubation at room temperature samples were analysed using a FACScan flow cytometer. A negative control of PBS and an IgM positive control of tissue culture supernatant from a IgM monoclonal antibody specific to the surface of Cryptosporidium oocysts were analysed with each batch of samples. The mean fluorescence intensities of the FITC anti the PE stained samples were recorded.

Samples of mouse serum diluted 1 in 500 in BSA-PBS were analysed using western blotting.

Production of Hybridomas

Mice were sacrificed, spleen cells dissected and fused with NS1 mouse myeloma cells and the resulting hybridomas cloned. A 50 μl volume of tissue culture supernatant from each hybridoma was mixed with 10 μl of oocyst suspension in PBS (containing approximately $1 \times 10^6$ oocysts). Samples were incubated at room temperature for 20 minutes and then mixed with 50 μl of goat anti-mouse antibody specific to both IgM and IgG antibodies and conjugated with FITC (diluted 1 in 100 with BSA-PBS) (Silenus, Melbourne). After a further 20 minutes incubation at room temperature samples were analysed using a FACScan flow cytometer. A negative control of tissue culture supernatant from a Dictyostelium-specific antibody (MUD62) and a positive control of tissue culture supernatant from a IgM monoclonal antibody specific to the surface of Cryptosporidium oocysts (CRY26) were analysed with each batch of samples. Hybridomas that produced a higher mean fluorescence (FL1) than the negative control were cloned and tested once more.

The immunological subclass of monoclonal antibody produced by clones was identified using the Sigma Immuno Type Kit.

Hybridoma Screening

Approximately 7–14 days after the fusion microwell plates were monitored for hybridoma growth. Hybridomas visible at 40× objective were marked, labelled and 100μl of tissue culture supernatant aseptically removed without disturbing the hybridomas at the bottom. All hybridomas were then refed with 100 μl of fresh medium for continued growth.

Initial Screen

To each 100 μl of hybridoma supernatant collected 10 μl of $1 \times 10^8$ oocysts was added and allowed to incubate for 15 minutes at room temperature. A second antibody anti-mouse FITC (Amrad) was then added (100 μl at 1:50 dilution) and incubated at room temperature for 15 minutes. Samples were then analysed by flow cytometry. Fluorescence intensity of the oocyst population was measured. High fluorescence seen on histogram indicated a positive for anti-Cryptosporidium antibodies. All positives were then marked and grown up for further culturing.

Secondary Screen

Once positive hybridomas had been culture into 12 well microtitre plates they were then tested for IgM or IgG antibody class. A 100 μl sample of each positive was placed in two separate tubes. To each tube 10 μl of $1 \times 10^8$ oocysts was added and incubated for 15 minutes at room temperature. To each duplicate tube 100 μl of prediluted FITC labelled, anti-IgG (Zymed 61-6011), or FITC labelled anti-IgM (Sigma F-9259) was added and allowed to incubate at room temperature for 15 minutes. Each sample was then analysed by flow cytometry. High fluorescence of the oocyst population observed on a histogram, indicated a positive for the antibody subclass which would later be confirmed.

Subclass Confirmation

All positive hybridomas were confirmed for Isotype by a commercially available (Serotec) haemagglutination assay, which employs sheep erythrocytes conjugated with an antibody which specifically recognises a mouse Ig isotype.

Analysis of Antibodies for Oocyst Staining in Water Samples

The effectiveness of mAbs for use in water samples was evaluated by flow cytometry. A 100 μl volume of supernatant was added to seeded samples. Seeded samples consisted of 50 μl water concentrate and 10 μl of a high oocyst seed. This was allowed to incubate at room temperature for 20 minutes. After this incubation 100 μl volume of anti-mouse FITC conjugated antibody (Silenus, 1:50) was added and incubated for a further 20 minutes. Samples were then analysed using flow cytometry. Data was analysed to determine which antibody produced the greatest separation between the immunoflurescent control (oocyst) population and the background fluorescent particles detected within water concentrates.

Functional Measurement of Avidity

Avidity of binding (affinity constant of whole antibody)of the FITC labelled anti-Cryptosporidium antibodies CRY104, CRY26 and a commercial anti-Cryptosporidium FITC-labelled antibody (Immunocel) were measured as follows. Antibodies of a known concentration where serially diluted out from a 20 μg concentration down for 20 two-fold dilutions. Each concentration of mAb was then incubated with $1 \times 10^7$ oocysts for 20 minutes at room temperature. A negative control of oocysts in PBS was also prepared to provide and end point for binding. Fluorescence (FL-1) values for each dilution were recorded and plotted. The value for 50% maximal binding to the oocysts for each mAb analysed was obtained. Assumptions were made that the total input antibody is very nearly the same as free antibody, therefore the dissociation constant (kd) is equal to this (50%) concentration. The affinity constant (ka) is then calculated as the reciprocal value.

Flow Cytometry

A FACScan flow cytometer was used for analysis of mouse serum and hybridomas. Logarithmic signals were used for all detectors. The threshold was set on side scatter at a value of 500. The detectors were set at the following levels of sensitivity: 200 for side scatter (SSC); E00 for forward scatter (FALS); 600 for the green fluorescence detector (FL1) and 600 for the red fluorescence detector (FL2). A region (R1) was defined on a dot plot of FALS versus SSC that enclosed single oocysts but not clumps of oocysts. Histograms of FL1 and FL2 were gated so that the only particles that appeared in region R1 would appear on the histograms. The mean value of FL1 and or FL2 from the histograms were recorded for 2000 oocysts from each sample analysed.

Sodium Dodecyl Sulphate-polyacrylamide Electrophoresis (PAGE)

Two hundred microlitres of oocyst s at $5 \times 10^7 – 10^8$ cells/ml were added to an equal volume of reducing buffer (composed of 975 μl 0.125 M Tris HCl/0.5% (w/v) SDS, 150 μl glycerol, 225 μl 10% (w/v) SDS, 150 μl 2-Mercaptoethanol and 20 μl Bromophenol Blue (0.25% w/v) and boiled for 3 minutes at 100° C.

This reduced sample was then run on a 12% polyacrylamide separating gel with a 5% stacking gel in a Biorad Miniprotean II cell apparatus. Proteins for high and low molecular weight markers (Novex) were run alongside the sample for approximately 45–60 minutes at 200 volts.

Western Blotting

Aliquots (100 µl) of oocyst suspension in PBS containing approximately $5 \times 10^7$ oocysts were mixed with 100 µl of reducing buffer and boiled for 2 minutes. The entire sample was loaded onto a 10% SDS slab gel and run at 150 V for 1 hour. A sample of prestained molecular weight markers (Novex) was included. Following SDS-PAGE, the proteins were transferred to nitrocellulose using a semi-dry electroblotting system and a discontinuous buffer system. The nitrocellulose was then cut into 2 mm wide strips and soaked in 2% (w/v) skimmed milk in PBS. The strips were then incubated with either mouse serum or hybridoma culture supernatant. Tissue culture supernatant from an IgM Cryptosporidium-specific monoclonal antibody was included as a positive control. Samples were incubated for 1 hour at room temperature. The nitrocellulose strips were then rinsed for 3×5 min in 3% (w/v) skimmed milk powder in PBS; then incubated for 1 h in a goat anti-mouse antibody (specific to both IgM and IgG antibodies) conjugated to horse radish peroxidase (HRP, Tao, Inc. Burlingame, Calif., USA). diluted to 1:1500 with 3% (w/v) skimmed milk powder in PBS. Strips were then washed for 3×5 min in PBS and developed using a fresh solution of 4CN substrate and finally washed extensively under running tap water for at least 20 min.

Water Samples

Samples (10 L) of untreated surface water were collected from locations around Australia and concentrated using a flocculation technique (Vesey et al. 1993a). A composite untreated surface water sample was prepared by mixing aliquots of samples from 15 different sites. The sample was centrifuged at 3000 g for 10 min and the pellet resuspended in PBS. Aliquots (50 µl) of water sample concentrate were seeded with 10 µl of oocyst suspension (containing approximately 1000 oocysts) and mixed thoroughly. The samples were then mixed with 50 µl of tissue culture supernatant from a Cryptosporidium-specific monoclonal antibody and incubated for 20 minutes at room temperature. An aliquot (50 µl) of a FITC conjugated goat anti-mouse antibody (specific to both IgG and IgM antibodies)(Silenus) diluted 1 in 300 in PBS-BSA was then added to each sample and incubated for 20 minutes at room temperature. Samples were then analysed using flow cytometry.

ALTERNATIVE METHODS

To separate the oocyst walls from the sporozoites the oocysts can be freeze-thawed instead of excysted. A purification step such as immuno-magnetic separation, flow cytometry or density gradient separation is required to purify the oocyst walls away from the sporozoites. The present inventors have prepared cell wall samples by surface labelling whole oocysts with biotin and after excystation binding the cell walls to avidin-labelled magnetic beads.

One alternative approach would involve smashing the whole oocysts (sporozoites still inside) into small pieces and then using an immunological purification method such as immuno-magnetic separation or affinity chromatography.

Other alternative methods such as sonication could be used to break up the oocysts or the purified oocyst walls.

Antibody Comparison Tests

Cryptosporidium oocysts and Giardia Cysts

*Cryptosporidium parvum* oocysts were isolated from naturally infected calves as previously described. Oocysts were heat inactivated at 65° C. for 15 minutes. *Giardia lamblia* cysts were obtained formalin fixed from Waterborne. Inc. (New Orleans, USA). Cysts and oocysts were stored in phosphate buffered saline (0.01M phosphate, pH 7.3±0.2) (Oxoid) at 4° C.

Cryptosporidium-specific and Giardia-specific Antibodies

Seven Cryptosporidium-specific and four Giardia-specific mAbs were evaluated in this study, their supplier, fluorescent label and class of antibody are described in Table 3 and 4.

Concentrated Water Samples

Samples (10 L) of untreated surface water were collected from sites around Australia and concentrated by flocculation or filtration. A composite untreated water sample was prepared by mixing aliquots of samples from a range of different sites. The sample was centrifuged at 13,000 rpm for 10 min and the pellet resuspended in PBS. The volume of the sample was adjusted so that 100 µl of concentrate was equivalent to 5 litres of original untreated water. Samples were also prepared from different water types which include raw river, effluent, filtered and backwash. All samples were pre-filtered through a 38-micron stainless steel mesh filter prior to use.

Sample Preparation

Fluorebrite™ beads (Polysciences, Inc. Warrington, Pa. USA.) were used to standardise the assay. Tile beads were added at a high concentration into bovine serum albumin (BSA, Sigma Chemical Co, St Louis USA) (4% w/v) in PBS and azide (0.05% v/v). The same volume of beads was then added to every sample, making it possible to monitor the volume of concentrate analysed, by the number of beads detected. The volume of water concentrate analysed for each sample was then standardised by producing a result per bead analysed. Sample buffer for staining samples consisted of BSA (1% w/v) Tween20 (0.05%v/v) in PBS.

Antibody Concentrations

Figure 2:
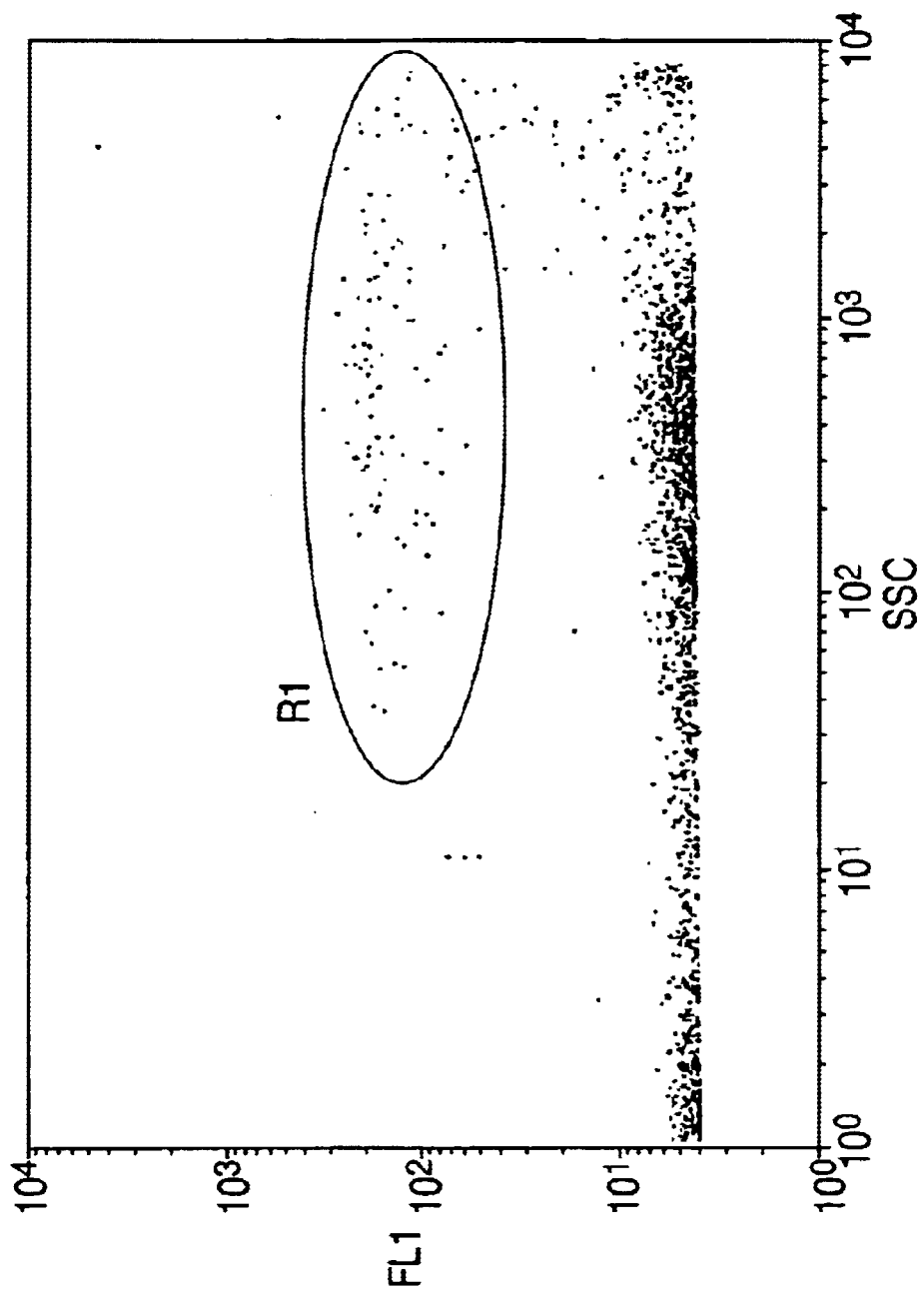
FIG. 2 shows flow cytometric analysis of Cryptosporidium oocysts seeded in a composite water concentrate. The fluorescent oocyst population is clearly separated from autofluorescent and extraneous particles bound non-specifically to antibody. The optimal concentration of mAb to use for water analysis needs to define a clear separation from background fluorescence as seen in this figure.

The optimal concentration or dilution of each antibody to be evaluated (Table 3 and 4) was firstly determined by flow cytometry. Serial dilutions for mAbs of unknown protein concentration were setup between 1:20 and 1:1.280 into appropriate sample buffer as described by the manufacturer. Those mAbs of known protein concentrations were set-up as serial dilutions between 8 µg/ml to 0.5 µg/ml. A 100 µl aliquot of each dilution was added to seeded samples. Seeded samples consisted of 50 µl water concentrate and 50 µl of a high oocyst or cyst seed. Samples were incubated at room temperature for 30 minutes and then analysed using flow cytometry. Data was analysed to determine which concentration of antibody produced the greatest separation between the immunofluorescent control (oocyst/cysts) population and the background fluorescent particles detected within water concentrates (FIG. 2).

Staining Water Samples

Following optimisation of antibody concentrations, each mAb was diluted to the appropriate concentration in sample buffer. All samples were prepared in 5 ml Falcon tubes. Positive controls were prepared consisting of 50 µl of the respective high seed. Water samples to be tested were prepared in triplicate and consisted of 50 µl water concentrate. Each mAb was added to controls and water samples to a total volume of 150 µl in sample buffer and mixed. After incubation at room temperature for 30 minutes samples were seeded with 20 µl aliquots of the Fluorbrite™ bead standard. Samples were then mixed by vortexing for 5 seconds and analysed.

The Hydrofluor mAb kit contains unconjugated Cryptosporidium-specific and Giardia-specific antibodies as well as an anti-mouse FITC conjugated antibody. The reagents were used as recommended in the manufacturers instructions.

Flow Cytometry

Figure 3:
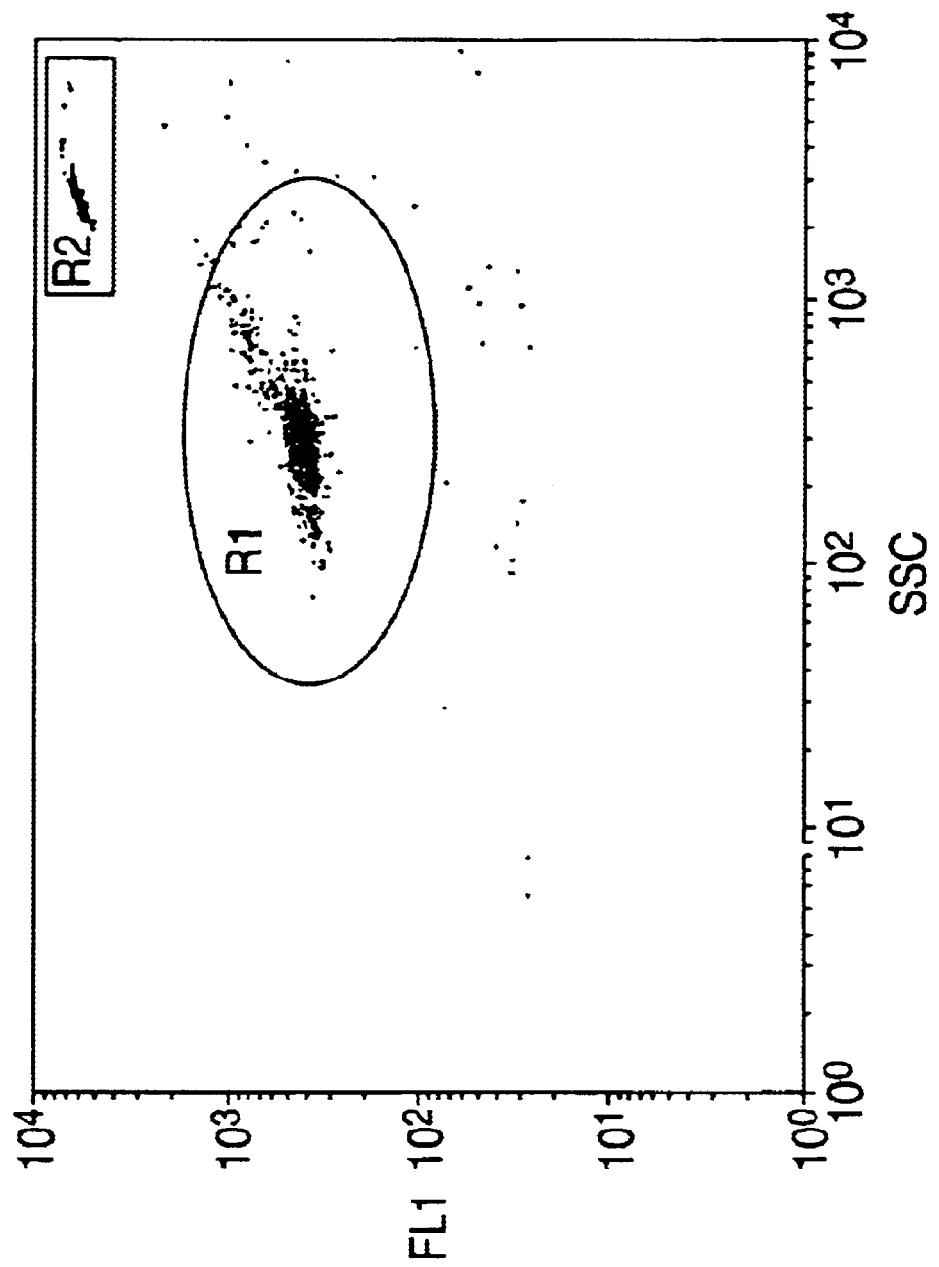
FIG. 3 shows flow cytometric analysis of a control sample of fluorescently stained Cryptosporidium oocysts. A default size elliptical region is centred on the main population of pure fluorescent oocysts for each antibody (R1). A polygon region is defined around the bead standard population (R2).

Comparison of Cryptosporidium and Giardia mAbs was carried out using a Becton-Dickinson FACScan flow cytometer (Becton-Dickinson, Lane Cove, NSW Australia). Sheath fluid consisted of undiluted Isoton II (Coulter Electronics, Brook Vale, NSW Australia). Detectors used were side angle light scatter (SSC) versus FL1 detector (green fluorescence). Voltages of detectors were set on 300 mV for SSC and 450 mV for all remaining detectors. Threshold was set on fluorescence detector 1 (FL1 ). Compensation was set at FL1-FL2 45%. Positive samples for each mAb were analysed first. Approximately 1,000 events were collected, and an ellipse region (R1 ) of default size was defined around the centre of the oocyst or cyst population (FIG. 2). A rectangular sort region (R2) was defined around the respective bead standard used. Once sort regions were defined, a sample of water concentrate was analysed to allow the operator to increase or decrease the discriminator until extraneous particles collected fluoresced just below R1 (FIG. 3). Once all regions were defined 5,000 events were collected for every sample. It was important that R1 be moved to the centre of the oocyst or cyst population for each antibody evaluated as fluorescence varies between mAbs.

Data Analysis

Figure 4:
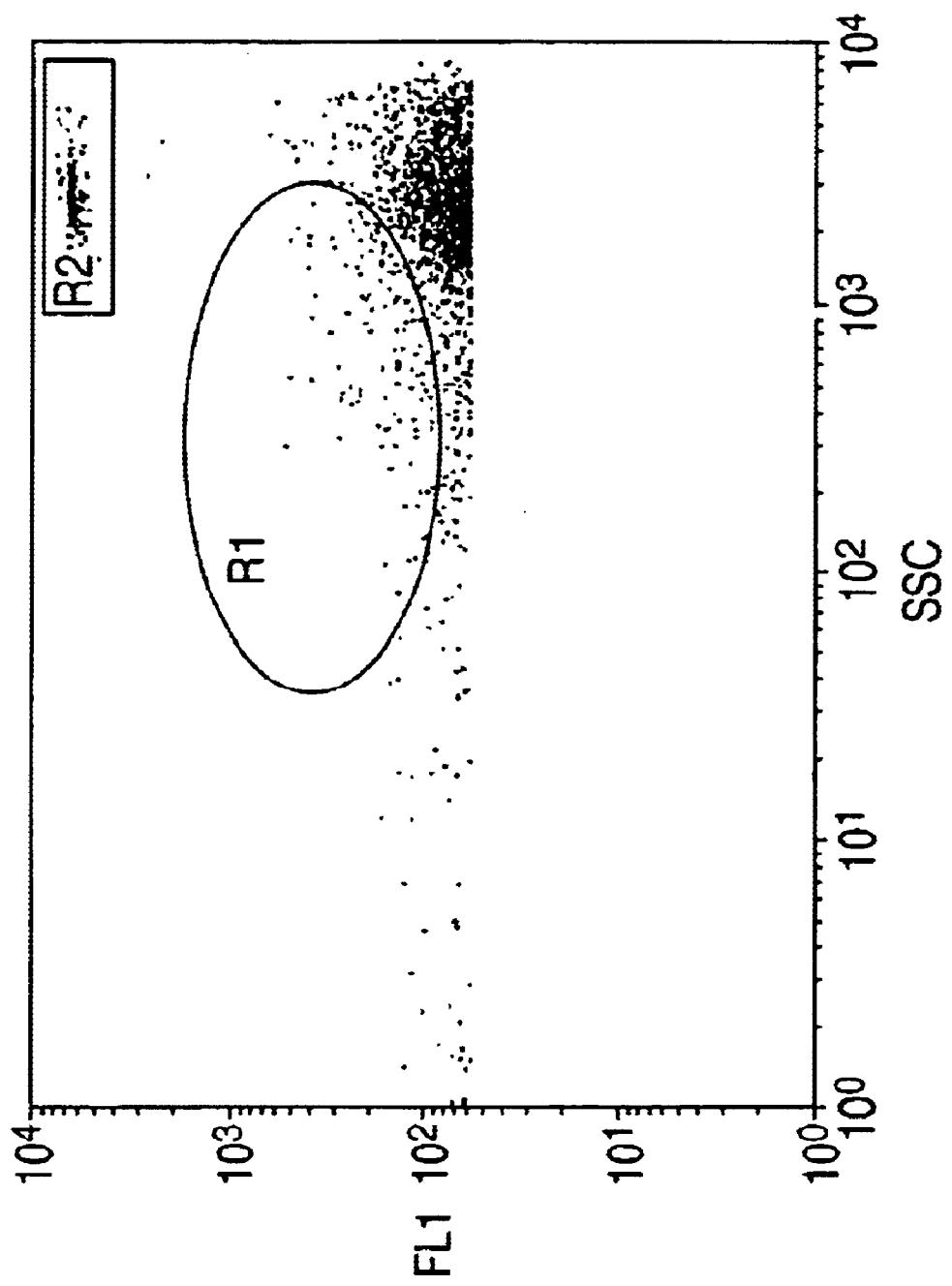
FIG. 4 shows flow cytometric analysis of a water concentrate containing no oocysts or cysts. The regions are those from FIG. 2 for each mAb examined. The number of particles within the oocysts or cyst region (R1) contain both autofluorescent and non-specifically bound particles. The number of particles in R1 are divided by the number of beads analysed (R2). The result is a ratio of non-specific binding comparable between antibodies.

Data analysis was carried out using LYSIS II software obtained from Becton-Dickinson, (Lane Cove, NSW Australia). Bivariate dot-plots defining SSC versus FL1 were used for analyses (FIGS. 3 and 4). Regions were defined as above. To enumerate the number of beads detected, a sort rectangle (R2) was defined around the bead population. This region was determined by analysis of a control sample consisting of beads and oocysts/cysts (FIG. 3). The specificity of each mAb was calculated in terms of a non-specific binding ratio by dividing tie number of events collected in R1 by R2.

Statistical Analysis

Data interpretation was performed using Microsoft Excel™ 4.0 and the Analysis Toolpack™ Add-in. The hypothesis that the means from different samples were equal was tested using analysis of variance (ANOVA). Using a significance level of 5% ($p<0.05$), the critical values for the F-statistic were calculated and compared to that obtained from the ANOVA. RESULTS Analysis of Mouse Serum Flow cytometric analysis of mouse serum revealed a large immunological response to the surface of Cryptosporidium oocysts in group E mice (Table 1). Twenty-one days after the second immunisation both IgM and IgG Cryptosporidium-specific antibodies were detected in the serum of group E mice. Oocysts stained with serum from group E mice fluoresced very brightly even when the serum was diluted to 1 in 10,000 (Table 1). The fluorescence of oocysts stained with serum from group W mice before and 21 days after the second immunisation were not significantly ($p>0.05$) different indicating that the immunisation did not cause the production of antibodies specific to the surface of Cryptosporidium oocysts. No antibodies specific to the surface of Cryptosporidium oocysts were detected in the serum of group W mice. The slight difference between the results for group W and group E mice prior to immunisation was most probably due to variation in the sensitivity of the instrument on different days.

TABLE 1

Comparison of the fluorescence intensity of *Cryptosporidium* oocysts stained with serum (diluted 1 in 1000) from group E and W mice and then stained with an anti-IgG or an anti-IgM fluorescently labelled antibody. Serum was tested prior to immunisation and then 21 days after the second immunisation.

| mouse number | IgG specific antibody | | IgM specific antibody | |
| --- | --- | --- | --- | --- |
| | Pre-immunisation | Post-immunisation | Pre-immunisation | Post-immunisation |
| E1 | 12 | 1117 | 12 | 111 |
| E2 | 9 | 460 | 11 | 121 |
| E3 | 10 | 195 | 11 | 74 |
| E4 | 10 | 1762 | 13 | 258 |
| E5 | 12 | 550 | 12 | 33 |
| W1 | 36 | 39 | 16 | 17 |
| W2 | 45 | 32 | 27 | 14 |
| W3 | 36 | 37 | 27 | 13 |
| W4 | 42 | 30 | 25 | 27 |
| W5 | 47 | 40 | 16 | 15 |
| Positive* control (IgM) | 42 | | 978 | |
| Negative Control | 27 | | 17 | |

ND - not determined
*a IgM monoclonal antibody specific to Cryptosporidium was used as a positive control. A IgG positive control was not available.

Hybridomas

Mouse number 4 from group E was sacrificed and the spleen cells fused with mouse myeloma cells. Screening of the resulting 230 clones identified six clones that were producing Cryptosporidium-specific antibody. Five of the clones (clones P9F1, P6G7, P11, P11D5 and P7D5) were found to be producing IgM antibody specific to the surface of Cryptosporidium oocysts. One clone (CRY104) was producing IgG1 antibody specific to the surface of Cryptosporidium oocysts.

Additional fusions of spleen cells from mice in group E have produced a large number of hybridomas specific for the specific to the surface of Cryptosporidium oocysts. Further IgG1 antibodies produced by these hybridomas have been characterised. This further demonstrated that the methods according to the present invention are particularly suitable to produce useful IgG1 antibodies specific to the surface of Cryptosporidium oocysts.

Fusions were not attempted with nice from group W because of the poor immunological response to Cryptosporidium that was observed.

Evaluation of Monoclonal Antibodies

Results of flow cytometric analysis of water samples seeded with oocysts and stained with some of the Cryptosporidium-specific monoclonal antibodies are presented in FIG. 1. Note the differences in the position of the population of oocysts along the Y axis. The oocyst population is closer to the top of the dotplot due for the sample stained with 8C12 (CRY104) than for any of the other samples. This is because the oocysts are fluorescing more brightly in this sample than any other sample. The fluorescence of the debris particles (below the oocysts) is not brighter in the 8C12 (CRY104) sample than in the unstained control. The separation between the oocysts and the debris particles is greatest in the 8C12 (CRY104) stained sample. This suggests that this antibody is most useful for staining Cryptosporidium oocysts in water samples. In comparison, the sample stained with 6G7 shows in increase in the fluorescence of some the debris particles (to the right of the oocysts) when compared to the unstained control. This is due to this antibody binding to some of the debris particles and suggests that this antibody may not be useful for staining Cryptosporidium oocysts in water samples.

Flow cytometric analysis of serum from mice immunised with intact purified oocyst walls (group WI mice) revealed no difference in the brightness of Cryptosporidium oocysts stained with serum collected before or after immunisation (Table 2). Similar results were observed when using both IgM specific and IgG specific second antibodies. In comparison, when oocysts were stained with the serum from group WP mice there was a difference in the fluorescence intensity of the oocysts stained with post immunisation serum and those stained with pre-immunisation serum. Results were similar for oocysts stained with both IgG specific and IgM specific secondary antibodies.

TABLE 2

Comparison of the fluorescence intensity of *Cryptosporidium* oocysts stained with serum (diluted 1 in 100 or 1 in 1000) from group WI and group WP mice and then stained with an anti-IgG or an anti-IgM fluorescently labelled antibody. Serum was tested prior to immunisation and then 21 days after the second immunisation.

| mouse number | IgG specific antibody | | IgM specific antibody | |
| --- | --- | --- | --- | --- |
| | Pre-immunisation | Post-immunisation | Pre-immunisation | Post-immunisation |
| [1]WI1 | 36 | 39 | 16 | 17 |
| WI2 | 45 | 32 | 27 | 14 |
| WI3 | 36 | 37 | 27 | 13 |
| WI4 | 42 | 30 | 25 | 27 |
| WI5 | 47 | 40 | 16 | 15 |
| [2]WP1 | [3]230 | 248 | 404 | 420 |
| WP2 | 231 | 518 | 405 | 514 |
| WP3 | 229 | 306 | 403 | 475 |
| WP4 | 233 | 290 | 410 | 417 |
| WP5 | 232 | 350 | 407 | 603 |

[1]WI - mice immunised with intact purified oocyst walls. Serum was diluted 1 in 1000.
[2]WP - mice immunised with small pieces of purified oocyst walls. Serum was diluted 1 in 100.
[3]Results of the two groups of mice are not directly comparable. Serum was not tested at the same dilution for both groups of mice. Different second antibodies were used to test the group W mice and the group WP mice.

Antibody Comparison Tests

When concentrated water samples were stained with mAbs directed to either Cryptosporidium or Giardia there was a significant ($p<0.05$) increase in the number of fluorescent particles observed with the stained, compared with unstained samples (Table 5 and 6). Differences were observed between different antibodies with respect to the immunofluorescent staining, with increases in fluorescent particles detected between mAbs. The IgG1 antibody CRY104 resulted in significantly ($p<0.05$) lower levels of non-specific binding by the fluorescent mAb to extraneous particles in water, than when staining with antibodies of the IgM or IgG3 subclass (Table 5). The IgG1 antibody G203 produced specifically for water analysis of Giardia, resulted in significantly less fluorescent background particles than when staining with antibodies produced for faecal analysis including an IgG1 (Table 6).

Specific antibodies (both Giardia and Cryptosporidium) were selected for evaluation of the effect of mAbs on staining different water types. Statistically different levels ($P<0.05\%$) of non-specific binding of particles to antibodies were observed between different water types for both Giardia and Cryptosporidium analysis (Table 7 and 8). The variation observed following staining with an IgG3 was higher between waters than the variation observed by the IgG1 mAb (Table 7). Greater variation in non-specific binding was seen with Hydrofluor™ mAb compared with G203 (Table 8) thus significant differences in the level of binding between mAbs for every water type was observed.

TABLE 3

Cryptosporidium-specific monoclonal antibodies evaluated.

| Antibody | Antibody Type | Supplier |
| --- | --- | --- |
| CRY104 | IgG1 FITC conjugate | MUCAB* |
| CRY26 ™ | IgM FITC conjugate | MUCAB* |
| CRY212 | IgM FITC conjugate | MUCAB* |
| Crypto-Cell | IgM FITC conjugate | CelLab, Australia |
| Crypto-a-glo ™ | IgM FITC conjugate | Waterborne. Inc. USA |
| Immucell ™ | IgG3 FITC conjugate | Immucell, Portland. USA |
| Hydrofluor ™ | IgM Not conjugated | Meridian, ENSYS Inc. USA |

*Macquarie University Centre for Analytical Biotechnology

TABLE 4

Giardia-specific monoclonal antibodies evaluated.

| Antibody | Antibody Type | Supplier |
| --- | --- | --- |
| G203 | IgG1 FITC conjugate | MUCAB* |
| Giardia-Cell | IgM FITC conjugate | CelLab, Australia |
| Giardia-a-glo ™ | IgG1 FITC conjugate | Waterborne. Inc. USA |
| Hydrofluor ™ Combo | Giardia IgG Not conjugated + Crypto IgG | Meridian, ENSYS Inc. USA |

*Macquarie University Centre for Analytical Biotechnology

TABLE 5

Comparison of the level non-specific binding to Cryptosporidium-specific mAbs

| Antibody | Non-specific Binding ratio* |
| --- | --- |
| CRY104 | 0.045 ± 0.013 |
| CRY26 | 0.623 ± 0.023 |
| CRY212 | 0.112 ± 0.034 |
| Crypto-Cell | 0.177 ± 0.034 |
| Crypto-a-glo ™ | 0.980 ± 0.125 |
| Immucell ™ | 0.155 ± 0.013 |
| Hydrofluor ™ | 0.159 ± 0.058 |
| Unstained | 0.033 ± 0.010 |

Results are the means of 3 separate analyses.
*Arbitrary scale developed for Cryptosporidium analysis (see M&M) Statistical difference ($p < 0.05$) by ANOVA

TABLE 6

Comparison of the level of non-specific binding to Giardia specific mAbs

| Antibody | Non-specific Binding ratio* |
| --- | --- |
| G203 | 0.029 ± 0.002 |
| Giardia-Cell | 0.163 ± 0.024 |
| Giardia-a-glo ™ | 0.201 ± 0.032 |
| Hydrofluor ™ | 0.044 ± 0.005 |
| Unstained | 0.020 ± 0.002 |

Results are the means of 3 separate analysis.
*Arbitrary scale developed for Giardia Analysis (see M&M) Statistical difference ($p < 0.05$) by ANOVA

TABLE 7

Evaluation of the level of non-specific binding of Cryptosporidium specific mAbs in different water concentrates.

| | Treatment mean ± SD | | |
|---|---|---|---|
| Water Type | Unstained control | CRY104 | Immucell ™ |
| Raw | 0.023 ± 0.002 | 0.023 ± 0.001 | 3.294 ± 0.327 |
| Backwash | 0.023 ± 0.003 | 0.020 ± 0.006 | 0.440 ± 0.049 |
| Raw | 0.021 ± 0.003 | 0.020 ± 0.004 | 0.385 ± 0.016 |
| Backwash | 0.022 ± 0.002 | 0.087 ± 0.038 | 0.233 ± 0.052 |
| Effluent | 0.035 ± 0.006 | 0.085 ± 0.01 | 1.801 ± 0.093 |
| Backwash | 0.023 ± 0.004 | 0.277 ± 0.031 | 0.869 ± 0.154 |
| Raw | 0.022 ± 0.006 | 0.025 ± 0.005 | 1.391 ± 0.036 |
| Raw | 0.036 ± 0.006 | 0.099 ± 0.013 | 0.651 ± 0.047 |
| Backwash | 0.023 ± 0.004 | 0.031 ± 0.002 | 0.156 ± 0.027 |
| Filtered | 0.026 ± 0.007 | 0.027 ± 0.002 | 0.166 ± 0.015 |

Statistical difference (p < 0.05) by ANOVA, N = 3

TABLE 8

Evaluation of the level of non-specific binding of Giardia specific mAbs in different water concentrates.

| | Treatment mean ± SD | | |
|---|---|---|---|
| Water Type | Unstained control | G203 | Hydrofluor ™ |
| Raw | 0.022 ± 0.002 | 0.048 ± 0.007 | 0.645 ± 0.01 |
| Backwash | 0.022 ± 0.003 | 0.034 ± 0.005 | 0.669 ± 0.008 |
| Raw | 0.020 ± 0.003 | 0.025 ± 0.002 | 0.696 ± 0.022 |
| Backwash | 0.021 ± 0.003 | 0.214 ± 0.094 | 14.63 ± 4.58 |
| Effluent | 0.032 ± 0.007 | 0.007 ± 0.001 | 1.021 ± 0.075 |
| Backwash | 0.021 ± 0.003 | 0.081 ± 0.014 | 10.36 ± 1.547 |
| Raw | 0.021 ± 0.006 | 0.023 ± 0.003 | 0.062 ± 0.005 |
| Raw | 0.031 ± 0.006 | 0.070 ± 0.022 | 1.637 ± 0.096 |
| Backwash | 0.022 ± 0.004 | 0.036 ± 0.009 | 0.111 ± 0.016 |
| Filtered | 0.024 ± 0.006 | 0.024 ± 0.003 | 0.043 ± 0.004 |

Statistical difference (p < 0.05) by ANOVA, N = 3

Evaluation of the number of fluorescent particles within a water concentrate before and after immunofluorescent staining revealed that with all mAbs tested there was significantly (p<0.05) higher numbers of fluorescent particles following staining. There was, however, a large variation in the number of fluorescent particles after staining with different mAbs. Analysis of different classes of mAbs revealed that staining with the IgG1 mAbs generally resulted in less fluorescent particles than staining with IgM and IgG3 mAbs.

Variation in the background fluorescence observed is largely due to the type of antibody used for the assay. The primary immune response to an antigen induces the production of IgM. Immunoglobulin M antibodies exist as large mAbs containing ten binding sites, with a greater chance of binding non-specifically to particles compared with IgG. The surface of oocysts and cysts contain carbohydrates that induce the production of low affinity IgM and IgG3. Immunoglobulin G1 mAbs are generally produced following repeated exposure to an antigen. Isotype switching occurs from IgM to IgG, resulting in higher affinity mAbs containing two identical binding sites more specific to the antigen they are produced to. Specificity of the IgM, CRY212 that was developed for water analysis was greater than commercial mAbs that were produced for clinical applications such as faecal analysis. This trend was observed following Giardia analysis of IgG1 mAbs, with G203 having higher affinity than Giardia-a-glo™.

Comparison of different water types revealed a significant difference in the non-specific binding ratio between waters. Variation was observed following staining with IgG1 mAbs (CRY104 and G203), however, the range of non-specific binding to different water types was significantly reduced over the other mAbs examined. The degree of variation in non-specific binding was significant with backwash samples displaying a diverse range in background fluorescence between a ratio of 0.111 and 14.63 for non-specific binding of the Hydroflor mAb. Thus, some water concentrates contain particles that have a much higher chance of binding to certain mAbs, however, for all water types the IgG1 mAbs caused the least increase in the number of fluorescent particles detected.

mAbs produced specifically for water analysis have a high affinity for cysts and oocysts over extraneous particles present within water concentrates. Immunoglobulin G1 are smaller mAbs that bind specifically to antigenic sites that they are produced to with little background interference. Production of new IgG1 mAbs to different antigenic sites on cysts or oocysts may enable the development of highly specific assays for Cryptosporidium and Giardia detection within environmental samples.

Table 9

Comparison of the fluorescence intensity of Cryptosporidium oocysts stained with serum of three dilutions (1:1000, 1:10,000, 1:100,000) from the mouse groups E (Extract), W (Walls) oocyst control (OC-mice injected with whole oocysts) or negative control (C) and then stained with an anti-IgG or all anti-IgM fluorescently labelled antibody. Data was calculated by subtracting the fluorescent value (arb) obtained from second serum samples after two immunisations from the negative serum samples prior to immunisation.

| | IgM Specific Antibody | | | IgG Specific Antibody | | |
|---|---|---|---|---|---|---|
| | 1:1000 | 1:10,000 | 1:100,000 | 1:1000 | 1:10,000 | 1:100,000 |
| Extract Mouse 1 | 280 | 129 | 64 | 353 | 370 | 229 |
| Extract Mouse 2 | 283 | 115 | 96 | 220 | 259 | 172 |
| Extract Mouse 3 | 278 | 129 | 90 | 67 | 84 | 73 |
| Extract Mouse 4 | 319 | 151 | 108 | 354 | 425 | 279 |
| Extract Mouse 5 | 45 | 92 | 99 | 103 | 324 | 44 |
| Walls Mouse 1 | 3 | 30 | 19 | −68 | −13 | 28 |
| Walls Mouse 2 | −3 | 36 | 2 | 29 | −31 | 10 |
| Walls Mouse 3 | 18 | 0 | 4 | 41 | 52 | 16 |
| Walls Mouse 4 | 38 | 38 | −3 | 24 | −3 | −4 |
| Walls Mouse 5 | 22 | 16 | 15 | 3 | −11 | 27 |
| Oocyst Control 1 | 432 | 240 | 115 | 2 | −18 | 13 |
| Oocyst Control 2 | 339 | 189 | 26 | −53 | −5 | 42 |
| Oocyst Control 3 | 438 | 228 | 69 | 48 | 45 | 2 |
| Oocyst Control 4 | 581 | 457 | 235 | 124 | 46 | 57 |
| Oocyst Control 5 | 210 | 75 | 37 | 21 | 43 | 43 |
| Control | 0 | 0 | 0 | 0 | 0 | 0 |

Western Blot Examination of Serum Samples and mAbs

A large amount of immunostained bands where observed in western blots carried out on mouse serum from each of the three immunisation groups (E, W, and OC). The oocyst control mouse group (OC) and extract mouse group (E) showed banding from >200 kD down to 40 kD with no distinct difference in banding patterns. The wall mouse group (W) showed unique banding only in the mid range between 100 kD and 160 kD. mAbs analysed by western blot showed.some unique banding patterns although all recognised two distinct bands, one at 200 kD and the other at 40 kD.

Functional Measurement of Avidity

TABLE 10

Shows the functional measurement of Avidity.

| Monoclonal Antibody | Subclass | ka (affinity constant of whole antibody) |
|---|---|---|
| CRY104 | IgG1 | $7 \times 10^8$ mol$^{-1}$ |
| CRY26 | IgM | $3 \times 10^8$ mol$^{-1}$ |
| Immucell ™ | IgG3 | $6 \times 10^7$ mol$^{-1}$ |

During the course of the immunisation program mice were monitored for both IgM and IgG levels in serum. The oocyst control group demonstrated a high IgM response with little or no IgG. This would suggest that there is no memory in the immune response (i.e. shift to IgG response) and that each immunisation is seen as a new antigen.

This may be due to *C. parvum* oocysts containing complex polysaccharide structures which do not require help of T-Lymphocytes to stimulate B-Cells into antibody production. Thus resulting in less isotype switching and reduced affinity maturation in mAbs produced. Hence less specific IgM antibodies dominate the immune response.

The oocyst walls group (W) showed no immune response. This is probably due to the large size and structure of the whole oocyst wall which may have a desensitising effect on the immune response. The fact that no immune response was seen in the oocyst wall group would suggest that with no sporozoites present a decrease in immunogenicity is obtained.

The oocyst extract group elicited strong IgM and IgG responses. IgM responses, however, were not as strong as in the oocyst control group, again suggesting that sporozoites are more antigenic than the oocyst wall and are characteristic of the self limiting nature of Cryptosporidium. It appears that the SDS digestion breaks up the oocyst wall and exposes more epitopes for an immune response. After removing the spoiozoites and breaking up the oocyst wall structure into smaller complexes the oocyst wall or extract becomes an extremely immunogenic antigen as shown from the strong immune response seen in the extract mice. After further immunisations in extract mice the IgG response further increased as for a typical immunisation program. This was not observed in the Control or Wall group, which showed dominant IgM response or no response respectively.

From the western blot analysis, extract and oocyst control groups share a similar banding pattern, with extract mice showing a more definitive banding pattern with one lower distinct band unshared (40 kD).

Measurement of the antibody avidity was made and compared to other anti-Crypto antibodies. The affinity constant for the IgG1 whole antibody was calculated to be 7*10E8 molE-1, which is a least double that of the other antibodies tested (Table 10). This indicates that CRY104 is at least twice as effective at binding to Cryptosporidium at a constant concentration than the other antibodies tested, and forms a stronger bond to the epitope. It was found that the binding efficiency of CRY104 facilitates more effective staining of Cryptosporidium at lower concentrations than other commonly used antibodies.

CONCLUSIONS

A strong immunological response to the surface of Cryptosporidium oocysts was produced by immunising mice with a partially purified sample of the outer layer of the oocyst wall. Immunising mice with purified oocyst walls did not produce a strong immunological response. This would suggest that there is either immune suppression by a component of the oocyst wall or that the natural presentation of the surface antigens on the oocyst walls does not produce an immunological response. The present inventors have overcome this lack of an immunological response to the surface of Cryptosporidium oocysts by partially purifying the surface antigens Fusion of spleen cells from one mouse immunised with the purified sample of the outer layer of the oocyst wall resulted in six (6) hybridomas that produce antibody that is specific to the surface of the oocyst wall. One of these six antibodies is of the IgG1 immunological subclass, the remaining five antibodies are of the IgM subclass. The IgG1 antibody appears to be superior to the IgM antibodies for staining Cryptosporidium oocysts in water samples. Mice immunised with purified Cryptosporidium oocysts walls do not produce a strong immunological response to the surface of Cryptosporidium oocysts. If, however, the purified oocysts walls are broken up into small pieces, then a strong response is produced in both the IgG and IgM immunological subclasses. Mice immunised with such a procedure would also be suitable for producing monoclonal antibodies of the IgG1 subclasses.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of producing isolated IgG1 subclass antibodies reactive to the surface of Cryptosporidium oocysts, the method comprising:

(a) pretreating Cryptosporidium oocysts with a reagent so as to remove the surface layer of the oocysts to form an oocysts antigen preparation;

(b) separating the oocysts from the oocyst antigen preparation so as to obtain a separated oocyst antigen preparation free from sporozoite antigens and capable of eliciting a detectable IgG1 immune response in an animal to the surface of the oocyst;

(c) immunizing an animal with the separated oocyst antigen preparation so as to elicit an IgG1 response in the animal; and (d) obtaining from the animal IgG1 antibodies reactive to the surface of Cryptosporidium oocysts.

2. The method according to claim 1 wherein the reagent is a detergent.

3. The method according to claim 2 wherein the detergent is sodium dodecyl sulphate (SDS).

4. The method according to claim 3 wherein the pretreating comprises boiling the oocysts in the presence of SDS to generate the oocyst antigen preparation.

5. The method according to claim 4 wherein the boiling of the oocysts is for at least one hour in the presence of 0.5% (w/v) SDS.

6. The method according to claim 1 wherein the reagent is selected from the group consisting of urea, detergents, including Triton X-100 and nonident, enzymes, including chitinase, oxidising agents, including sodium hypochlorite, sodium periodate, and ozone; and reducing agents, including mercaptol ethanol and 1,1,1-trichloro-2,2-bis[4-chlorophenyl]ethane.

7. The method according to claim 1 wherein the preparation of step (c) further includes one or more adjuvants.

8. The method according to claim 1 wherein the animal is a mouse.

9. A method of producing isolated IgG1 subclass antibodies reactive to the surface of Cryptosporidium oocysts, the method comprising:
   (a) separating at least a portion of the Cryptosporidium oocysts wall from the internal sporozoites to form an oocyst-wall preparation free from sporozoite antigens;
   (b) treating the separated oocyst-wall preparation so as to obtain an isolated oocyst wall antigen preparation free from sporozoite antigens capable of eliciting a detectable IgG1 immune response in an animal to the surface of the oocyst;
   (c) immunizing an animal with the isolated oocyst wall antigen preparation so as to elicit an IgG1 immune response in the animal; and
   (d) obtaining from the animal IgG1 antibodies reactive to the surface of Cryptosporidium oocysts.

10. The method according to claim 9 wherein the separation of the oocyst wall from the internal sporozoites comprises inducing the oocysts to excyst followed by immuno-separation of the oocyst wall components.

11. The method according to claim 9 wherein the separation of the oocyst wall from the internal sporozoite comprises inducing the oocyst to excyst followed by separation of the wall components by means selected from the group consisting of centrifugation, flow cytometry, density gradient separation, precipitation, immuno-labelling, ligand-binding, biotin-labelling with separation by avidin, and chromatographic separation.

12. The method according to claim 10 wherein inducing the oocyst to excyst comprises freeze-thawing or physically breaking up by crushing, sonication, or grinding the oocyst.

13. The method according to claim 9 wherein the treating step (b) comprises physically breaking up the cell wall.

14. The method according to claim 9 wherein the preparation of step (c) further includes one or more adjuvants.

15. The method according to claim 9 wherein the animal is a mouse.

16. An isolated IgG1 antibody reactive to the surface of Cryptosporidium oocysts produced by the method according to claim 1.

17. The antibody according to claim 16 wherein the antibody is a monoclonal antibody.

18. An isolated IgG1 antibody reactive to the surface of Cryptosporidium oocysts produced by the method according to claim 9.

19. The antibody according to claim 18 wherein the antibody is a monoclonal antibody.

20. An isolated IgG1 antibody reactive to the surface of Cryptosporidium oocysts, wherein the antibody has the oocysts binding and affinity characteristics of antibody CRY104.

21. The antibody according to claim 20 wherein the IgG1 monoclonal antibody is produced by hybridoma CRY104.

22. The hybridoma clone CRY104.

23. A method of producing isolated IgG1 subclass antibodies reactive to the surface of Cryptosporidium oocysts, the method comprising:
   (a) pretreating Cryptosporidium oocysts with a reagent that removes surface layer antigens from the oocysts to form an oocyst surface antigen preparation;
   (b) separating the oocysts from the oocyst surface antigen preparation to obtain an isolated oocyst surface antigen preparation free from sporozoite antigens;
   (c) immunizing an animal with the isolated oocyst surface antigen preparation so as to elicit an IgG1 immune response in the animal; and
   (d) recovering from the animal IgG1 antibodies reactive to the surface of Cryptosporidium oocysts.

24. The method according to claim 23 wherein the reagent is a detergent.

25. The method according to claim 24 wherein the detergent is sodium dodecyl sulphate (SDS).

26. The method according to claim 25 wherein the pretreating comprises boiling the oocysts in the presence of SDS to generate the oocyst surface antigen preparation.

27. The method according to claim 26 wherein the boiling of the oocyst is for at least one (1) hour in the presence of 0.5% (w/v) SDS.

28. The method according to claim 25 wherein the reagent is selected from the group consisting of urea, detergents, including Triton X-100 and nonident, enzymes, including chitinase, oxidising agents, including sodium hypochlorite, sodium periodate, and ozone; and reducing agents including mercaptol ethanol and 1,1,1-trichloro-2,2-bis(4-chlorophenyl)ethane.

29. The method according to claim 23 wherein the preparation of step (c) further includes one or more adjuvants.

30. A method of producing isolated IgG1 subclass antibodies reactive to the surface of Cryptosporidium oocysts, the method comprising:
   (a) separating the Cryptosporidium oocyst wall from internal sporozoites to form an oocyst-wall preparation free from sporozoite antigens;
   (b) immunizing an animal with the oocyst-wall preparation so as to elicit an IgG1 immune response in the animal; and
   (c) recovering from the animal IgG 1 antibodies reactive to the surface of Cryptosporidium oocysts.

31. The method according to claim 30 wherein the separation of the oocyst wall from the internal sporozoites comprises inducing the oocyst to excyst followed by separation of the oocyst wall components from the released sporozoites.

32. The method according to claim 31 wherein the separation of the oocyst wall component from the released sporozoite comprises means selected from the group consisting of immuno-separation, centrifugation, flow cytometry, density gradient separation, precipitation, immuno-labelling, ligand-binding, biotin-labelling with separation by avidin, and chromatographic separation.

33. The method according to claim 31 wherein inducing the oocyst to excyst comprises freeze-thawing or physically breaking up by crushing, sonication or grinding the oocyst.

34. The method according to claim 30 wherein the treating step (b) comprises physically breaking up the oocyst wall.

35. The method according to claim 30 wherein the oocyst wall antigen preparation in step (c) further comprises one or more adjuvants.

36. A method of producing isolated IgG1 subclass antibodies reactive to the surface of Cryptosporidium oocysts, the method comprising:
   (a) separating the Cryptosporidium oocyst wall from internal sporozoites to form an oocyst wall preparation free from sporozoite antigens;
   (b) treating the separated oocyst wall preparation to obtain an isolated oocyst wall antigen preparation free from sporozoite antigens;
   (c) immunizing an animal with the oocyst wall antigen preparation to elicit an IgG1 immune response in the animal; and
   (d) recovering from the animal IgG1 antibodies reactive to the surface of Cryptosporidium oocysts.

* * * * *